United States Patent
Lin et al.

(10) Patent No.: US 12,201,630 B2
(45) Date of Patent: Jan. 21, 2025

(54) NALTREXONE INJECTABLE SUSTAINED RELEASE FORMULATION

(71) Applicant: Alar Pharmaceuticals Inc., Taichung (TW)

(72) Inventors: Tong-Ho Lin, Taichung (TW); Yung-Shun Wen, Taichung (TW); Ying-Ting Liu, Taichung (TW); Zhi-Rong Wu, Taichung (TW)

(73) Assignee: Alar Pharmaceuticals Inc., Taichung (TW)

( * ) Notice: Subject to any disclaimer, the term of this patent is extended or adjusted under 35 U.S.C. 154(b) by 825 days.

(21) Appl. No.: 17/414,992

(22) PCT Filed: Dec. 26, 2019

(86) PCT No.: PCT/CN2019/128663
§ 371 (c)(1),
(2) Date: Jun. 17, 2021

(87) PCT Pub. No.: WO2020/135576
PCT Pub. Date: Jul. 2, 2020

(65) Prior Publication Data
US 2022/0062277 A1    Mar. 3, 2022

Related U.S. Application Data

(60) Provisional application No. 62/785,259, filed on Dec. 27, 2018.

(51) Int. Cl.
*A61K 31/485* (2006.01)
*A61K 9/00* (2006.01)
(Continued)

(52) U.S. Cl.
CPC .......... *A61K 31/485* (2013.01); *A61K 9/0019* (2013.01); *A61K 47/32* (2013.01); *A61P 25/30* (2018.01); *A61P 25/36* (2018.01)

(58) Field of Classification Search
CPC .... A61K 31/485; A61K 9/0019; A61K 47/32; A61K 9/0024; A61K 9/08; A61K 47/10;
(Continued)

(56) References Cited

U.S. PATENT DOCUMENTS 6,569,449 B1    5/2003  Stinchcomb et al.
2009/0246265 A1 * 10/2009 Stinchcomb ......... A61K 9/7061
424/449

FOREIGN PATENT DOCUMENTS

WO    2005/107753        11/2005
WO    WO-2017100863 A1 *  6/2017  ........... A61K 31/485

OTHER PUBLICATIONS

Makadia et al., Poly Lactic-co-Glycolic Acid (PLGA) as Biodegradable Controlled Drug Delivery Carrier, Polymers (Basel), 3, pp. 1377-1397 (Year: 2012).*

(Continued)

*Primary Examiner* — Jeffrey S Lundgren
*Assistant Examiner* — Alexander K. Showalter
(74) *Attorney, Agent, or Firm* — Amin, Turocy & Watson, LLP

(57) ABSTRACT

Provided is an injectable sustained release pharmaceutical formulation, including 3-acyl-naltrexone or a pharmaceutically acceptable salt thereof, a biocompatible organic solvent, and optionally a biocompatible polymeric material. Also provided is a method for treating opioid use disorder or alcoholism, including administering the injectable sustained release pharmaceutical formulation to a subject in need thereof. The pharmaceutical formulation provides a sustained release profile after one single injection, and the plasma levels of naltrexone in minipigs could provide a sustained release for 2 months.

6 Claims, 4 Drawing Sheets

(51) Int. Cl.
  *A61K 47/32*    (2006.01)
  *A61P 25/30*    (2006.01)
  *A61P 25/36*    (2006.01)
(58) Field of Classification Search
  CPC ........ A61K 47/14; A61K 47/18; A61K 47/20;
           A61K 47/22; A61K 47/34; A61P 25/32;
                      A61P 25/30; A61P 25/36
  See application file for complete search history.

(56) References Cited

OTHER PUBLICATIONS

Mottu et al. Organic Solvents for Pharmaceutical Parenterals and Embolic Liquids: A Review of Toxicity Data, PDA J. Pharm. Sci. & Tech., 54, pp. 456-469 (Abstract only) (Year: 2000).*
International Search Report and Written Opinion for International Application No. PCT/CN2019/128663 mailed on Mar. 26, 2020, 8 pages.
Akala, et al. "Studies on in vitro availability, degradation, and thermal properties of naltrexone-loaded biodegradable microspheres", Drug Dev Ind Pharm., vol. 37, No. 6, Jun. 30, 2011, pp. 673-684.
Valiveti, et al. "In vivo evaluation of 3-O-alkyl ester transdermal prodrugs of naltrexone in hairless guinea pigs", Journal of Controlled Release, vol. 102, Nov. 5, 2004, pp. 509-520.

* cited by examiner

NALTREXONE INJECTABLE SUSTAINED RELEASE FORMULATION

TECHNICAL FIELD

The present disclosure relates to injectable sustained release pharmaceutical formulations, especially injectable sustained release pharmaceutical formulations comprising naltrexone derivatives. The present disclosure also relates to a method for treating opioid use disorder (OUD) or alcohol use disorder (AUD, also known as alcoholism) by administrating the injectable sustained release pharmaceutical formulations to a subject in need thereof.

BACKGROUND

Naltrexone, 17-(cyclopropylmethyl)-4,5α-epoxy-3,14-dihydroxymorphinan-6-one, is a derivative of thebaine, which belongs to the family of opioid alkaloids. The structure of naltrexone is shown as Formula I below with a molecular weight of 341.40.

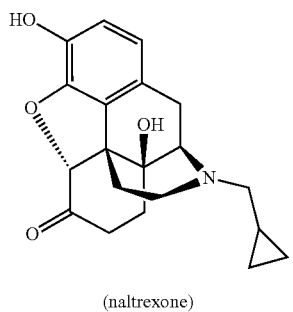

(naltrexone)

As a competitive antagonist with high affinity for the μ-receptor, naltrexone has greater potency to compete with other full agonists, such as morphine or heroin, etc. With an antagonistic effect twice than that of naloxone, naltrexone is indicated for the treatment of opioid use disorder and alcoholism in several dosage forms, e.g. Revia (oral tablet) and Vivitrol (intramuscular injection). The clinical dose ($C_{max}$) of Vivitrol is 380 mg, which is 3 to 4-folds of the daily oral dosing with naltrexone (i.e., 50 mg) over 28 days. In addition, various products of naltrexone hydrochloride have been disclosed, which include combinations of naltrexone hydrochloride and other compounds, e.g. Contrave (oral tablet, 8 mg naltrexone hydrochloride and 90 mg bupropion hydrochloride), Embeda (oral capsule, in a 25:1 ratio of naltrexone hydrochloride and morphine sulfate), and Troxyca ER (oral capsule, 1.2 mg naltrexone hydrochloride and 10 mg oxycodone hydrochloride). These products are indicated for obesity or moderate to severe pain. As a non-selective opioid antagonist without agonist activity, naltrexone is used in combination with a full opioid agonist (e.g., methadone) or a partial opioid agonist (e.g., buprenorphine) to reduce opioid abuse for a course of treatment.

In previous studies, various naltrexone derivatives were disclosed. Among them, it is more common to modify the 3-hydroxyl group by forming ester bond linkages. These ester derivatives are synthesized and compared with naltrexone and the hydrochloride salt thereof. In 1987, Hussain et al. published an article about 3-alkyl ester derivatives of naltrexone in *J. Pharm. Sci.* (1987), 75(5), 356-358, as shown in Formula II below, where R represents anthranilate, acetylsalicylate, benzoate, or pivalate. These derivatives are provided as prodrugs in an attempt to improve physiochemical characteristics of naltrexone and increase oral bioavailability in dogs.

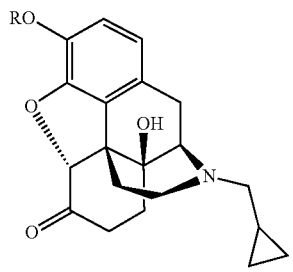

Stinchcomb et al. disclosed in *J. Pharm. Sci.* (2002), 91(12), 2571-2578 a naltrexone-3-alkyl ester prodrug shown in Formula II above, with R representing acetate, propanoate, butanoate, pentanoate, hexanoate, or heptanoate. These naltrexone derivatives improved physiochemical characteristics of naltrexone and increased the human skin permeation rate in vitro. The extent of naltrexone regeneration in the intact skin ranged from 28 to 91%.

Valiveti et al. disclosed in *J. Control. Release* (2005), 102(2), 509-520 in vivo transdermal delivery in hairless guinea pigs of three 3-O-alkyl ester prodrugs of naltrexone shown in Formula II above, with R representing acetate, propionate, or hexanoate. The pharmacokinetic parameters for naltrexone and the 3-O-alkyl ester prodrugs of naltrexone were detected after intravenous administration and topical application of transdermal therapeutic systems (TTS) in guinea pigs. The results of the in vivo studies showed mean steady-state plasma concentrations of naltrexone. These naltrexone plasma concentrations were maintained for 48 hours.

In addition, several C3-esterified naltrexone derivatives and the applications thereof have been disclosed in different patents. For example, European Patent No. 2064215 B1 issued to Zynerba Pharmaceuticals Inc. described naltrexone prodrugs shown in Formula II above with R representing pivaloate, isovalerate, 2-ethylbutyrate, isobutyrate, isopropyloxycarbonoate, or tertiarybutyloxycarbonoate. Naltrexone and the prodrugs thereof as opioid antagonists were used in combination with opioid agonists such as buprenorphine or the prodrugs thereof, which were transdermally administered for treating opioid use disorder or alcoholism.

Naltrexone ester derivatives were also disclosed in U.S. Pat. No. 6,569,449 B1 issued to University of Kentucky Research Foundation. In this U.S. patent, naltrexone was modified with esters shown in Formula II above with R representing valerate or heptanoate. The in vitro diffusion study depicted about an eight-fold increase in the naltrexone cumulative amount when the prodrug, valeroyl-naltrexone, was transdermally delivered through the skin sample in comparison to naltrexone. This formulation for transdermal delivery of effective amount of naltrexone was used for the treatment of opioid use disorder and alcoholism.

There are a variety of sustained release designs for naltrexone indicated for the treatment of opioid use disorder and alcoholism. For example, Southern Research Institute developed an injectable naltrexone microsphere composition, which comprises naltrexone in a poly (D, L-lactide) matrix and a residual amount of ethyl acetate. This composition was also disclosed in U.S. Pat. No. 6,306,425 B1. In this U.S. patent, human subjects were injected intramuscularly with the formulations for clinical studies and showed that such administration of the formulations maintained a release profile of naltrexone over 31 days.

The technology of microsphere formulations was disclosed in several patents issued to Alkermes. For example, U.S. Pat. No. 6,264,987 B1 disclosed the controlled release microparticle products containing naltrexone and polymers with a selected molecular weight. In addition, U.S. Pat. No. 7,799,345 B2 disclosed an injectable suspension, which mixes naltrexone, microparticles and an aqueous injection vehicle, in which the injection vehicle consists of water, a viscosity enhancing agent, a wetting agent, and a tonicity adjusting agent. Furthermore, U.S. Pat. No. 7,919,499 B2 disclosed an injectable microsphere suspension of naltrexone, i.e., Vivitrex, which utilizes the proprietary technology of Medisorb. The formulation was used for treatment of alcoholism, and was administrated by intramuscular injection monthly.

BioCorRx Inc. developed a sustained release naltrexone implant, BICX102, which was used for the treatment of opioid use disorder and alcoholism. The implant could be surgically inserted into the upper arm of a patient, providing 3-month and 6-month release profiles. In addition, BioCorRx Inc. also developed an injectable naltrexone, BICX101. This formulation is an intramuscular or subcutaneous injectable suspension, which utilized TheraKine's patented micro-delivery technology, maintaining therapeutic plasma levels for up to 3 months. This technology was also disclosed in U.S. Patent Publication No. 2017/0065579 A1.

Akala et al. disclosed in *Drug Dev. Ind. Pharm.* (2011), 37(6), 673-684 a naltrexone-loaded poly(D,L-lactide-coglycolide) microsphere. In vitro availability studies showed that the drug is capable of sustained release for a duration of 30 to 150 days. The drug-delivery systems will be useful for patients with alcoholism.

Liu et al. disclosed in *Drug Dev. Ind. Pharm.* (2006), 32(1), 85-94 a naltrexone poly(lactide) microsphere, which was injected into the subcutaneous area of rats. The plasma levels in rats showed that naltrexone concentrations constantly exceeded 2 ng/mL for 28 days. The biodegradable depot systems may provide long-term treatment of opioid dependence. Sustained release formulations of naltrexone have been provided for treatment in the relevant field. However, there still exist disadvantages of these formulations, such as complicated manufacturing processes, inaccessible administration procedure, low drug loading and fluctuation of the releasing profile. Effective plasma concentration levels of Vivitrol in the clinical study were limited to only one month. This disclosure, therefore, provides formulations of naltrexone comprising 3-acyl-naltrexone derivatives with different therapeutic durations ranging from one week to several months for patients in need of various therapeutic treatment plans. For example, this disclosure provides formulations of naltrexone having sustained duration after one single injection for treating opioid use disorder or alcoholism.

SUMMARY

The present disclosure provides an injectable sustained release pharmaceutical formulation comprising 3-acyl-naltrexone derivative or a pharmaceutically acceptable salt thereof, and a biocompatible solvent.

In one embodiment of the present disclosure, the injectable sustained release pharmaceutical formulation further comprises a biocompatible polymeric material.

In one embodiment of the present disclosure, the pharmaceutically acceptable salt of the 3-acyl-naltrexone may be in a salt form of HCl, formate and acetate, but is not limited thereto.

The injectable sustained release pharmaceutical formulation of the present disclosure provides a sustained release of the prodrug of 3-acyl-natrexone for at least one week to several months. Therefore, the injectable sustained release pharmaceutical formulations of the present disclosure provide an accessible administration procedure, sustained release profile and long therapeutic duration.

The present disclosure also provides a method for treating opioid use disorder, comprising administering the injectable sustained release pharmaceutical formulation to a subject in need thereof.

The present disclosure also provides a method for treating alcoholism, comprising administering the injectable sustained release pharmaceutical formulation to a subject in need thereof.

Other aspects of the present disclosure will become apparent with attached drawings and following detailed descriptions.

DETAILED DESCRIPTION

Figure 1:
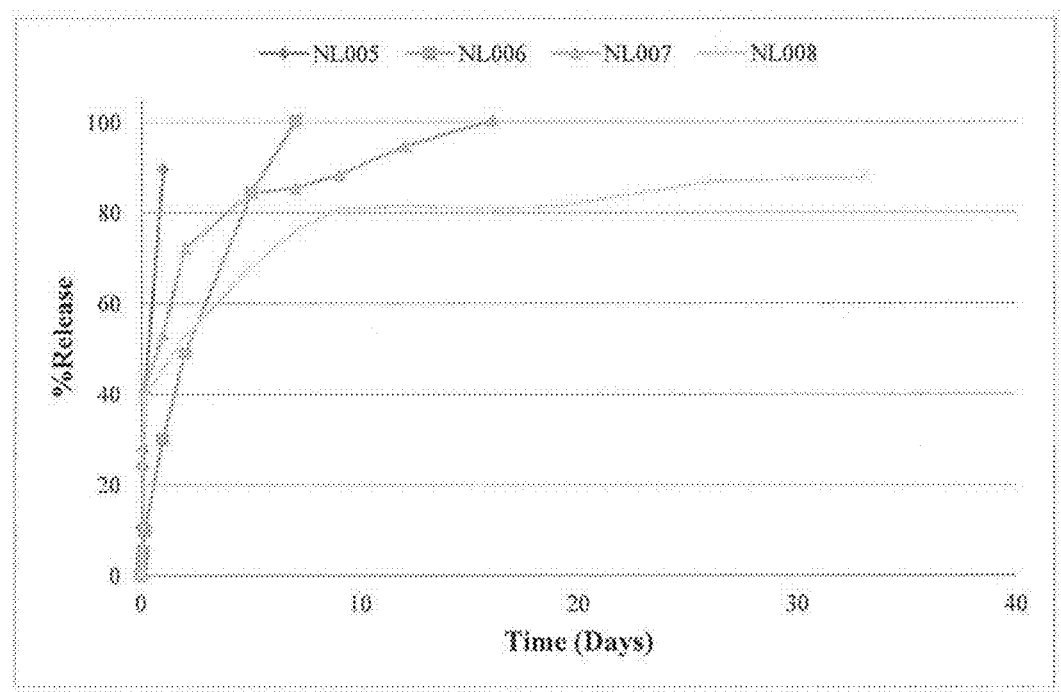
FIG. 1 shows in vitro dissolution profiles of the injectable sustained release pharmaceutical formulations containing various naltrexone derivatives in accordance with Example 2 of the present disclosure.

In one embodiment of the present disclosure, formulations of naltrexone derivatives that exhibit a long therapeutic duration after one single dose administration for treatment are provided. The treatment comprises opioid use disorder (OUD) and alcohol use disorder (AUD, also known as alcoholism).

In one embodiment of the present disclosure, an injectable sustained release pharmaceutical formulation comprises 3-acyl-naltrexone or a pharmaceutically acceptable salt thereof, and a biocompatible solvent. In one embodiment of the present disclosure, the injectable sustained release pharmaceutical formulation comprises 3-acyl-naltrexone or a pharmaceutically acceptable salt thereof in a lower limit of 1%, 5%, 10%, 15%, 20%, 25%, 30%, 35%, 40%, 45% or 50% by weight, and the injectable sustained release pharmaceutical formulation comprises 3-acyl-naltrexone or a pharmaceutically acceptable salt thereof in an upper limit of 99%, 95%, 90%, 85%, 80%, 75%, 70%, 65%, 60%, 55% or 50% by weight, based on a total weight of the injectable sustained release pharmaceutical formulation. For example, the 3-acyl-naltrexone or a pharmaceutically acceptable salt thereof is present in an amount of between 1% and 99% by weight, between 1% and 90% by weight, between 5% and 90% by weight, between 5% and 80% by weight, between 10% and 70% by weight, or between 10% and 60% by weight, based on the total weight of the injectable sustained release pharmaceutical formulation.

In another embodiment of the present disclosure, the injectable sustained release pharmaceutical formulation is an injectable sustained release pharmaceutical polymer-based formulation comprising a biocompatible polymeric material. In one embodiment of the present disclosure, the injectable sustained release pharmaceutical formulation comprises the biocompatible polymeric material in a lower limit of 1%, 2%, 3%, 4%, 5%, 10%, 15%, 20%, 25%, 30%, 35%, 40%, 45% or 50% by weight, and the injectable sustained release pharmaceutical formulation comprises the biocompatible polymeric material in an upper limit of 95%, 90%, 85%, 80%, 75%, 70%, 65%, 60%, 55%, 50%, 45%, 40%, 35%, 30%, 25%, 20%, 15%, 10%, 9%, 8%, 7%, 6%, or 5% by weight, based on the total weight of the injectable sustained release pharmaceutical formulation. For example, the biocompatible polymeric material is present in an amount of between 1% and 10% by weight, between 1% and 8% by weight, between 3% and 8% by weight, or between 5% and 7% by weight, based on the total weight of the injectable sustained release pharmaceutical formulation.

In one embodiment of the present disclosure, the 3-acyl-naltrexone or a pharmaceutically acceptable salt thereof comprises an ester group formed between the 3-hydroxy (phenol) group of naltrexone and an alkylcarbonylation or arylcarbonylation (acylation) reagent.

In one embodiment of the present disclosure, the alkylcarbonylation or arylcarbonylation (i.e., acylation) reagent has a formula of R—CO—X, wherein R is an alkyl or aryl residue, which may be an acyl chloride, an acyl anhydride, or an acyl active ester. The alkyl portion of the alkylcarbonyl group may be a straight-chain or branched-chain alkyl group. In one embodiment, the alkyl portion may contain a suitable number of carbons, such as 1 to 20 ($C_1$-$C_{20}$), 1 to 12 ($C_1$-$C_{12}$), 1 to 10 ($C_1$-$C_{10}$), 1 to 6 ($C_1$-$C_6$), 1 to 5 ($C_1$-$C_5$), 1 to 4 ($C_1$-$C_4$) or 1 to 2 ($C_1$-$C_2$). Examples of the alkylcarbonyl (acyl) groups include, but are not limited to, acetyl, butyryl, valeryl, hexanoyl, decanoyl or lauroyl. The aryl portion of the arylcarbonyl group comprises an aryl group or an aryl-alkyl group, and the alkyl portion is as defined above. The aryl portion of the arylcarbonyl group may comprise a $C_6$-$C_{18}$ aromatic ring, such as a phenyl group or a naphthyl group. In another embodiment of the present disclosure, the pharmaceutically acceptable salt of the 3-acyl-naltrexone may be HCl, formate, acetate, pamoic acid, citric acid, tartaric acid and maleic acid, but is not limited thereto.

In one embodiment of the present disclosure, the 3-acyl-naltrexone may be synthesized by conventional methods. Naltrexone or its salt may be purchased from several commercial sources such as Sigma-Aldrich. To prepare a naltrexone derivative, naltrexone (or its salt) is made to react with an acyl chloride in the presence of a non-nucleophilic base (e.g., triethylamine) to form an ester bond. The product (3-acyl-naltrexone or 3-alkylcarbonyl-naltrexone) may be purified with conventional methods, such as column chromatography.

In one embodiment of the present disclosure, 3-acyl-naltrexone including 3-alkylcarbonyl-naltrexone or 3-arylcarbonyl-naltrexone or a salt thereof may be used as a prodrug, which is then converted into the parent compound, naltrexone, i.e., the pharmaceutically active compound.

In one embodiment of the present disclosure, the biocompatible solvent may be an organic solvent, such as N-methyl-2-pyrrolidone (NMP), ethyl acetate, ethanol (EtOH), butanol, 2-butanol, isopropanol (IPA), isobutanol, glycerin, benzyl benzoate (BnBzO), dimethyl sulfoxide (DMSO), propylene glycol (PG), dimethyl glycol, N,N-dimethylacetamide (DMAc), benzyl alcohol, an ester, an ether, an amide, a carbonate, a lactam, a sulfonyl, or a combination thereof. In one embodiment of the present disclosure, the biocompatible polymeric materials are used as excipients, such as poly (D, L-lactide) (PLA) and poly (D, L-lactide/glycolide) (PLGA). In one embodiment of the present disclosure, the PLA and the PLGA are in a molar ratio of 75:25. In another embodiment of the present disclosure, the PLA and the PLGA are in a molar ratio of 50:50.

In one embodiment of the present disclosure, the injectable sustained release pharmaceutical formulation is formulated for subcutaneous, intramuscular or intradermal injection.

Embodiments of the present disclosure will be further illustrated with the following examples. However, one skilled in the art would appreciate that these examples are provided for illustration only and that other modifications and variations are still possible without departing from the scope of this disclosure.

Example 1: Preparation of Naltrexone Derivatives

The naltrexone derivatives were synthesized using traditional methods as described below. Naltrexone HCl was mixed with dichloromethane in a 3-necked round-bottom flask to form a suspension, followed by placing in an ice bath for cooling. Triethylamine was then added slowly into the 3-necked round-bottom flask with stirring, followed by addition of acyl chloride having 1 to 20 carbons. Esterification reaction was performed under nitrogen atmosphere at ambient temperature. The reaction mixture was neutralized with a saturated sodium bicarbonate aqueous solution. The organic layer was washed with brine and then dried with sodium sulfate, followed by concentration under reduced pressure. The crude naltrexone derivative of 3-acyl-naltrexone was purified with silica gel column chromatography.

Example 2: Preparation of Injectable Sustained Release Pharmaceutical Formulations 15 wt % to 70 wt % of the naltrexone derivative was added into a glass vial and dissolved in one or a combination of two or more biocompatible organic solvents such as N-methyl-2-pyrrolidone (NMP), ethyl acetate, ethanol (EtOH), butanol, 2-butanol, isopropanol (IPA), isobutanol, glycerin, benzyl benzoate (BnBzO), dimethyl sulfoxide (DMSO), propylene glycol (PG), dimethyl glycol, N,N-dimethylacetamide (DMAc) and benzyl alcohol.

Alternatively, 15 wt % to 70 wt % of the naltrexone derivative and the biocompatible polymeric materials of (D, L-lactide) and poly (D, L-lactide/glycolide) in a molar ratio of 75:25 or 50:50 were added into a glass vial, and then dissolved in one or a combination of two or more biocompatible organic solvents such as N-methyl-2-pyrrolidone, ethyl acetate, ethanol, butanol, 2-butanol, isopropanol, isobutanol, glycerin, benzyl benzoate, dimethyl sulfoxide, propylene glycol, dimethyl glycol, N,N-dimethylacetamide and benzyl alcohol.

The mixture was stirred constantly at ambient temperature or heated slightly until all of the ingredients were dissolved. The obtained injectable sustained release pharmaceutical formulations are listed in Table 1 below.

TABLE 1

List of the injectable sustained release pharmaceutical formulations

| Formulation No | Naltrexone Derivative (wt %) | Organic Solvent (wt %) | Polymeric Material (wt %) |
|---|---|---|---|
| NL001 | Naltrexone hexanoate, 50% | BnBzO, 50% | — |
| NL002 | Naltrexone decanoate, 50% | BnBzO, 50% | — |
| NL003 | Naltrexone hexanoate, 50% | NMP, 50% | — |
| NL004 | Naltrexone decanoate, 50% | NMP, 50% | — |
| NL005 | Naltrexone acetate, 50% | NMP, 50% | — |
| NL006 | Naltrexone butyrate, 40% | NMP, 60% | — |
| NL007 | Naltrexone benzonate, 15% | NMP, 85% | — |
| NL008 | Naltrexone pivaloate, 20% | NMP, 80% | — |
| NL009 | Naltrexone pivaloate, 15% | DMAc, 85% | — |
| NL010 | Naltrexone hexanoate, 50% | DMAc, 50% | — |
| NL011 | Naltrexone isobutyrate, 20% | NMP, 80% | — |
| NL012 | Naltrexone acetate, 50% | DMAc, 50% | — |
| NL013 | Naltrexone acetate, 50% | DMSO, 50% | — |
| NL014 | Naltrexone acetate, 60% | EtOH, 40% | — |
| NL015 | Naltrexone acetate, 60% | IPA, 40% | — |
| NL016 | Naltrexone acetate, 15% | PG, 85% | — |
| NL017 | Naltrexone butyrate, 50% | DMAc, 50% | — |
| NL018 | Naltrexone butyrate, 15% | DMSO, 85% | — |
| NL019 | Naltrexone isobutyrate, 20% | DMAc, 80% | — |
| NL020 | Naltrexone hexanoate, 50% | NMP, 45% | PLA, 5% |
| NL021 | Naltrexone hexanoate, 50% | NMP, 45% | PLGA7525, 5% |
| NL022 | Naltrexone hexanoate, 50% | NMP, 45% | PLGA5050, 5% |
| NL023 | Naltrexone hexanoate, 50% | NMP, 40% | PLA, 10% |
| NL024 | Naltrexone hexanoate, 60% | NMP, 40% | — |
| NL025 | Naltrexone decanoate, 70% | NMP, 30% | — |
| NL026 | Naltrexone decanoate, 50% | NMP, 40% | PLA, 10% |
| NL027 | Naltrexone pivaloate, 30% | NMP, 70% | — |

Figure 2:
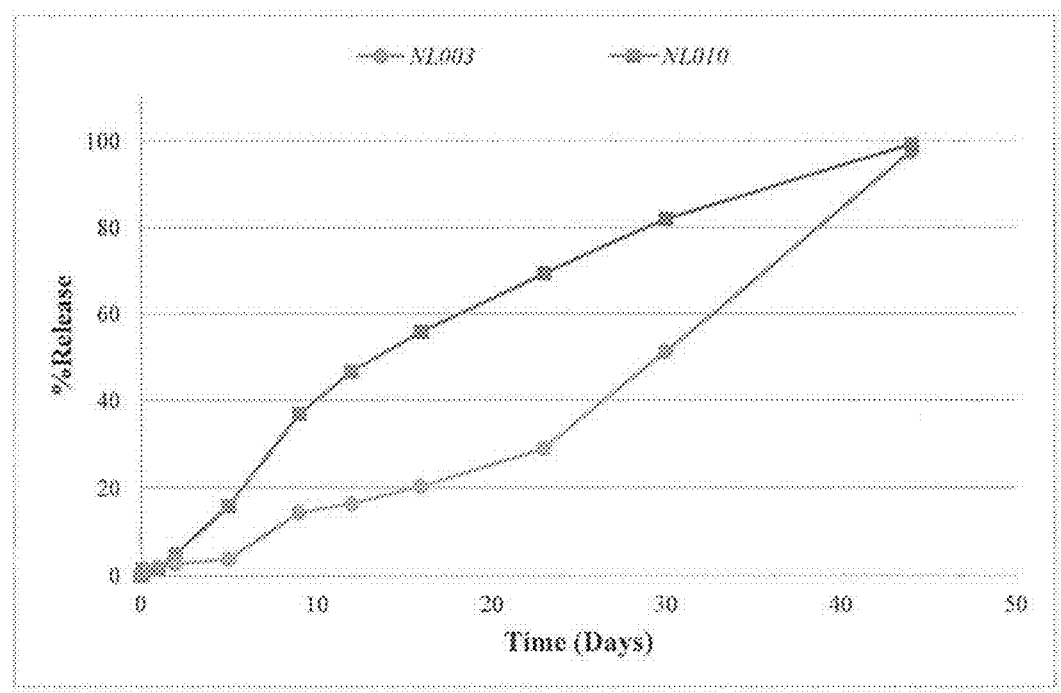
FIG. 2 shows in vitro dissolution profiles of the injectable sustained release pharmaceutical formulations containing naltrexone hexanoate dissolved in different organic solvents in accordance with Example 2 of the present disclosure.

Example 3: In Vitro Dissolution Test of the Injectable Sustained Release Pharmaceutical Formulations Each of the formulations NL003, NL005, NL006, NL007, NL008 and NL010 prepared in Example 2 was respectively assessed for its in vitro dissolution profile. Each of the formulations NL005, NL006, NL007 and NL008 was mixed with a dissolution medium of phosphate buffered saline comprising 0.1% sodium dodecyl sulfate and 0.02% sodium azide in a single tube, and each of the formulations NL003 and NL010 was mixed with a dissolution medium of phosphate buffered saline comprising 0.2% sodium dodecyl sulfate and 0.02% sodium azide in a single tube. Each of the tubes was shaking at 60 rpm in a 37° C. water bath. 1 mL of sample was removed from each of the tubes at specific time points and applied to HPLC for naltrexone derivatives and naltrexone free base analysis. Each of the tubes was refilled with 1 mL of a fresh dissolution medium. The profiles of dissolution rates of the formulations NL005, NL006, NL007 and NL008 were shown in Table 2 and FIG. 1, and those of the formulations NL003 and NL010 were shown in Table 3 and FIG. 2. The results showed that formulations NL003, NL006, NL007, NL008 and NL010 may sustainedly release naltrexone derivatives for one week to more than one month.

TABLE 2

Dissolution rates of formulations NL005 to NL008

| Time (days) | % Release | | | |
|---|---|---|---|---|
| | NL005 | NL006 | NL007 | NL008 |
| 0 | 0 | 0 | 0 | 0 |
| 0.042 | 10.78 | 2.77 | 24.90 | 25.81 |
| 0.083 | 24.02 | 5.26 | 28.62 | 29.75 |
| 0.167 | 40.92 | 9.87 | 41.78 | 39.73 |
| 1 | 89.57 | 30.00 | 53.27 | 45.59 |
| 2 | — | 49.05 | 72.14 | 52.76 |
| 5 | — | 84.35 | 84.40 | 68.14 |
| 7 | — | 100.36 | 85.39 | 76.04 |
| 9 | — | — | 88.35 | 80.68 |
| 12 | — | — | 94.67 | 81.43 |
| 16 | — | — | 100.46 | 80.89 |
| 19 | — | — | — | 81.38 |
| 26 | — | — | — | 86.81 |
| 33 | — | — | — | 87.76 |

TABLE 3

Dissolution rates of the formulations NL003 and NL010.

| Time (days) | % Release | |
|---|---|---|
| | NL003 | NL010 |
| 0 | 0 | 0 |
| 0.042 | 1.03 | 0 |
| 0.083 | 1.50 | 1.51 |
| 0.208 | 1.50 | 1.11 |
| 1 | 1.96 | 1.58 |
| 2 | 2.67 | 4.95 |
| 5 | 3.82 | 15.91 |
| 9 | 14.42 | 36.93 |
| 12 | 16.45 | 46.69 |
| 16 | 20.38 | 55.84 |
| 23 | 29.03 | 69.39 |
| 30 | 51.24 | 82.02 |
| 44 | 97.52 | 99.20 |

Figure 3:
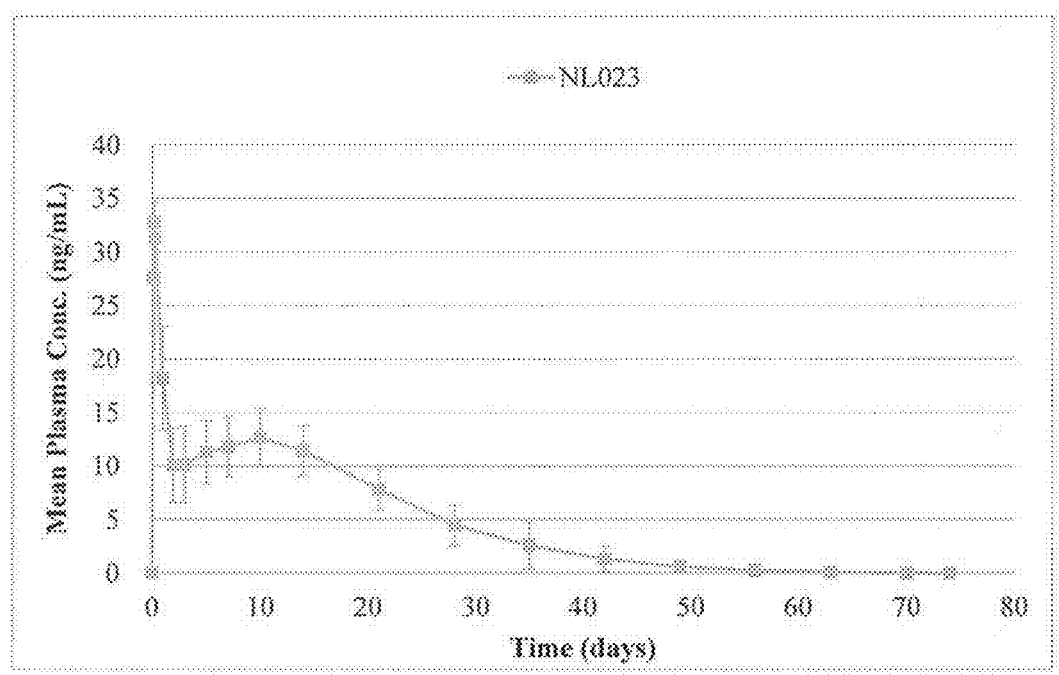
FIG. 3 shows mean plasma levels of naltrexone after subcutaneous injection of NL023 at the dose of 10.3 mg naltrexone/kg in minipigs, in accordance with embodiments of the present disclosure.
Figure 4:
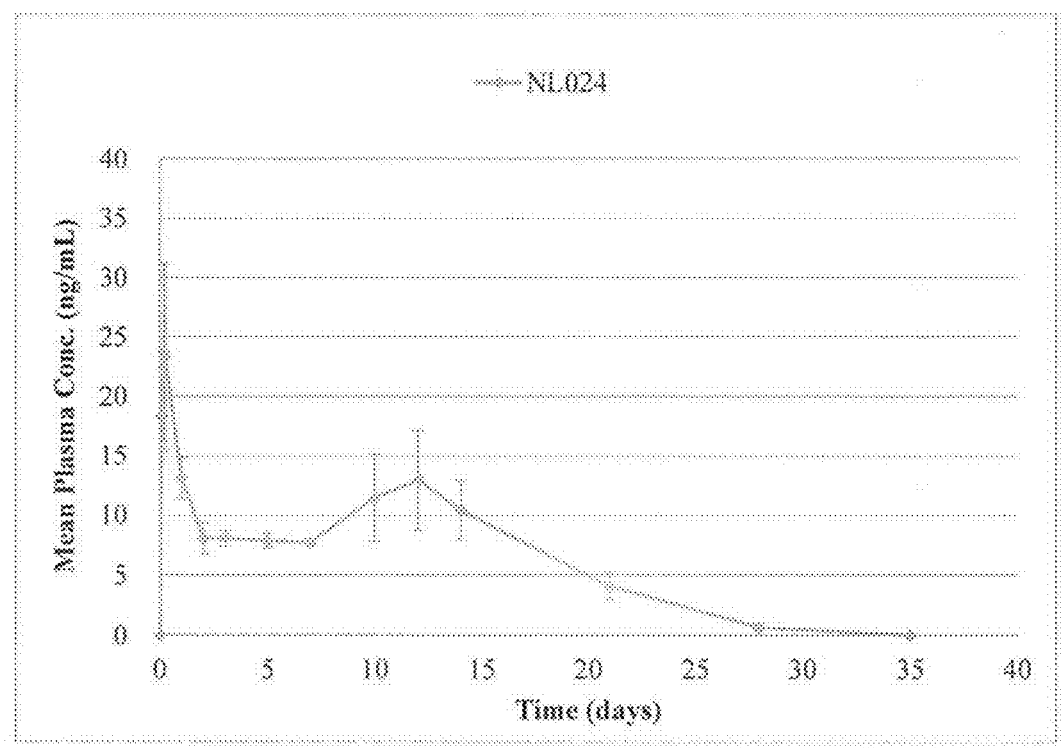
FIG. 4 shows mean plasma levels of naltrexone after subcutaneous injection of NL024 at the dose of 10.3 mg naltrexone/kg in minipigs, in accordance with embodiments of the present disclosure.

Example 4: Pharmacokinetic Profiles of the Injectable Sustained Release Pharmaceutical Formulations in Minipigs The formulations prepared in Example 2 were injected subcutaneously into male Lanyu minipigs at a dose of 10.3 mg naltrexone/kg. Blood samples were collected from external jugular veins at specific time points. Plasma samples were separated by centrifuge and stored in frozen conditions for later analysis. LC-MS/MS was used to analyze the concentrations of naltrexone in the plasma samples. The pharmacokinetic profile of the formulation NL023 was shown in Table 4 and FIG. 3. The results showed that formulation NL023 could provide sustained release of naltrexone for 2 months. The pharmacokinetic profile of the formulation NL024 was shown in Table 5 and FIG. 4. The results showed that formulation NL024 could provide sustained release of naltrexone for one month.

TABLE 4

Pharmacokinetic profile of the formulation NL023 in minipigs

| Time (days) | NL023 (10.3 mg/kg) | |
|---|---|---|
| | Mean (ng/ml) | S.D. (n = 3) |
| 0 | 0 | 0 |
| 0.083 | 27.60 | 2.36 |
| 0.167 | 32.77 | 1.85 |
| 0.25 | 31.20 | 1.08 |
| 1 | 18.17 | 4.80 |
| 2 | 10.09 | 3.48 |
| 3 | 10.13 | 3.59 |
| 5 | 11.30 | 2.93 |
| 7 | 11.81 | 2.78 |
| 10 | 12.65 | 2.68 |
| 14 | 11.46 | 2.39 |
| 21 | 7.84 | 1.96 |
| 28 | 4.48 | 1.89 |
| 35 | 2.59 | 2.16 |
| 42 | 1.33 | 1.18 |
| 49 | 0.60 | 0.47 |
| 56 | 0.26 | 0.27 |
| 63 | 0.09 | 0.08 |
| 70 | 0.03 | 0.05 |
| 74 | 0 | 0 |

TABLE 5

Pharmacokinetic profile of the formulation NL024 in minipigs

| Time (days) | NL024 (10.3 mg/kg) | |
|---|---|---|
| | Mean (ng/ml) | S.D. (n = 3) |
| 0 | 0 | 0 |
| 0.083 | 18.27 | 3.04 |
| 0.167 | 23.70 | 7.46 |
| 0.25 | 23.30 | 7.91 |
| 1 | 13.10 | 1.75 |
| 2 | 8.08 | 1.32 |
| 3 | 8.08 | 0.68 |
| 5 | 7.89 | 0.61 |
| 7 | 7.73 | 0.33 |
| 10 | 11.47 | 3.67 |
| 12 | 12.95 | 4.18 |
| 14 | 10.43 | 2.46 |
| 21 | 4.08 | 1.09 |
| 28 | 0.67 | 0.30 |
| 35 | 0 | 0 |

Figure 5:
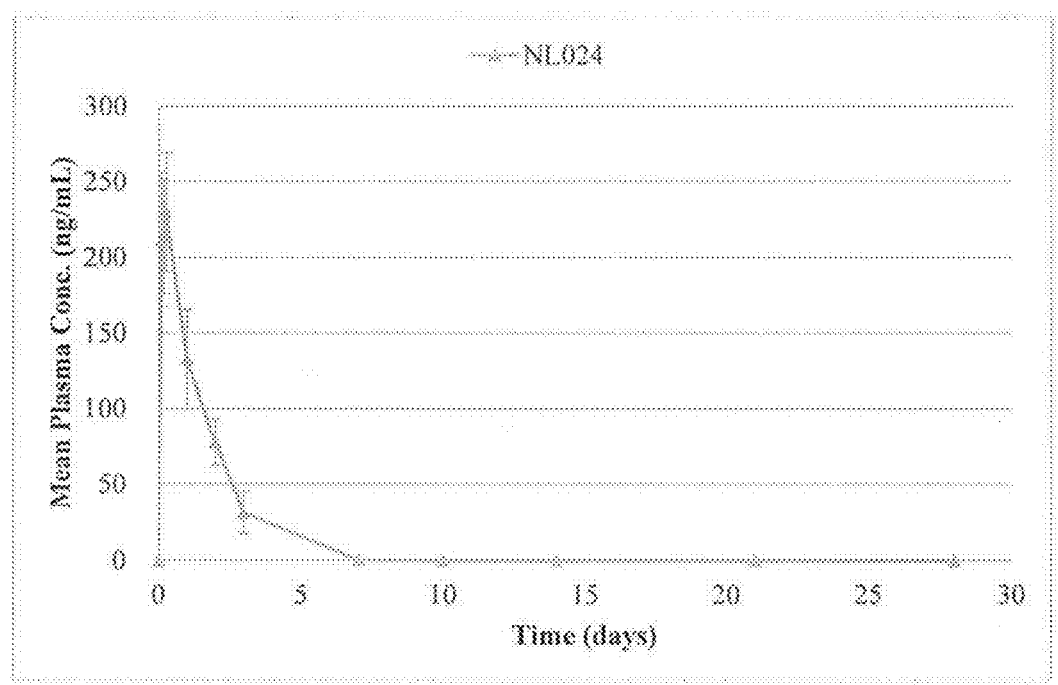
FIG. 5 shows mean plasma levels of naltrexone after subcutaneous injection of NL024 at the dose of 60 mg naltrexone/kg in rats, in accordance with embodiments of the present disclosure.
Figure 6:
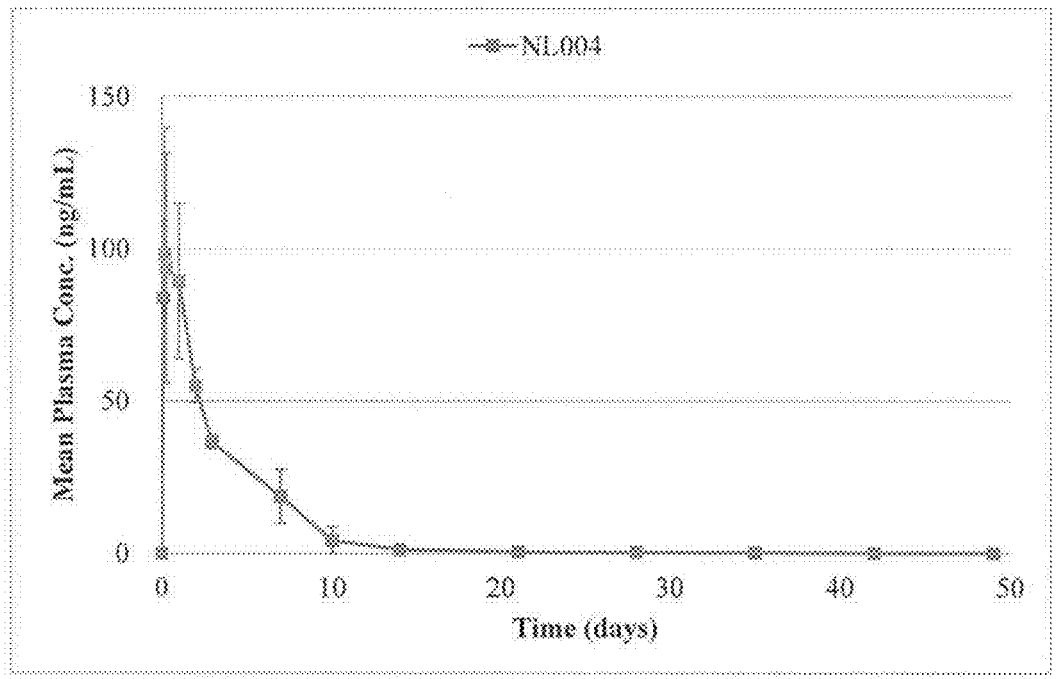
FIG. 6 shows mean plasma levels of naltrexone after subcutaneous injection of NL004 at the dose of 120 mg naltrexone/kg in rats, in accordance with embodiments of the present disclosure.

Example 5. Pharmacokinetic Profiles of the Injectable Sustained Release Pharmaceutical Formulations in Rats The formulations prepared in Example 2 were injected subcutaneously into male CD (SD) IGS rats at a dose of 60 and 120 mg naltrexone/kg. Blood samples were collected from tail veins at specific time points. Plasma samples were separated by centrifuge and stored in frozen conditions for later analysis. LC-MS/MS was used to analyze the concentrations of naltrexone in the plasma samples. The pharmacokinetic profile of the formulation NL024 was shown in Table 6 and FIG. 5. The pharmacokinetic profile of the formulation NL004 was shown in Table 7 and FIG. 6.

TABLE 6

Pharmacokinetic profile of the formulation NL024 in rats

| Time (days) | NL024 (60 mg/kg) | |
|---|---|---|
| | Mean (ng/ml) | S.D. (n = 4) |
| 0 | 0 | 0 |
| 0.083 | 211.75 | 44.21 |
| 0.167 | 213.75 | 38.06 |
| 0.25 | 230.00 | 39.45 |
| 1 | 132.55 | 33.03 |
| 2 | 77.68 | 15.36 |
| 3 | 31.68 | 13.75 |
| 7 | 0.37 | 0.42 |
| 10 | 0.14 | 0.06 |
| 14 | 0.09 | 0.04 |
| 21 | 0.10 | 0.09 |
| 28 | 0 | 0 |

TABLE 7

Pharmacokinetic profile of the formulation NL004 in rats

| Time (days) | NL004 (120 mg/kg) | |
|---|---|---|
| | Mean (ng/mL) | S.D. (n = 3) |
| 0 | 0 | 0 |
| 0.083 | 83.87 | 25.38 |
| 0.167 | 98.10 | 41.49 |
| 0.25 | 93.47 | 37.70 |
| 1 | 89.27 | 25.36 |
| 2 | 55.07 | 5.55 |
| 3 | 36.57 | 2.21 |
| 7 | 18.73 | 8.90 |
| 10 | 4.21 | 4.51 |
| 14 | 1.31 | 1.10 |
| 21 | 0.55 | 0.68 |
| 28 | 0.37 | 0.56 |
| 35 | 0.23 | 0.34 |
| 42 | 0.04 | 0.07 |
| 49 | 0 | 0 |

Example 6: In Vivo Releasing Profiles of the Injectable Sustained Release Pharmaceutical Formulations in Minipigs and Rats The pharmacokinetic data in minipigs and rats were analyzed for the area under curve during specific time point ($AUC_{0-t}$) and the area under the plasma concentration-time curve from time 0 extrapolated to infinity ($AUC_{0-\infty}$). The releasing percentage of naltrexone in the release profile was estimated by the ratio of $AUC_{0-t}$ to $AUC_{0-\infty}$.

$$\% \text{ Release} = \frac{AUC_{0-t}}{AUC_{0-\infty}} \times 100\%$$

Figure 7:
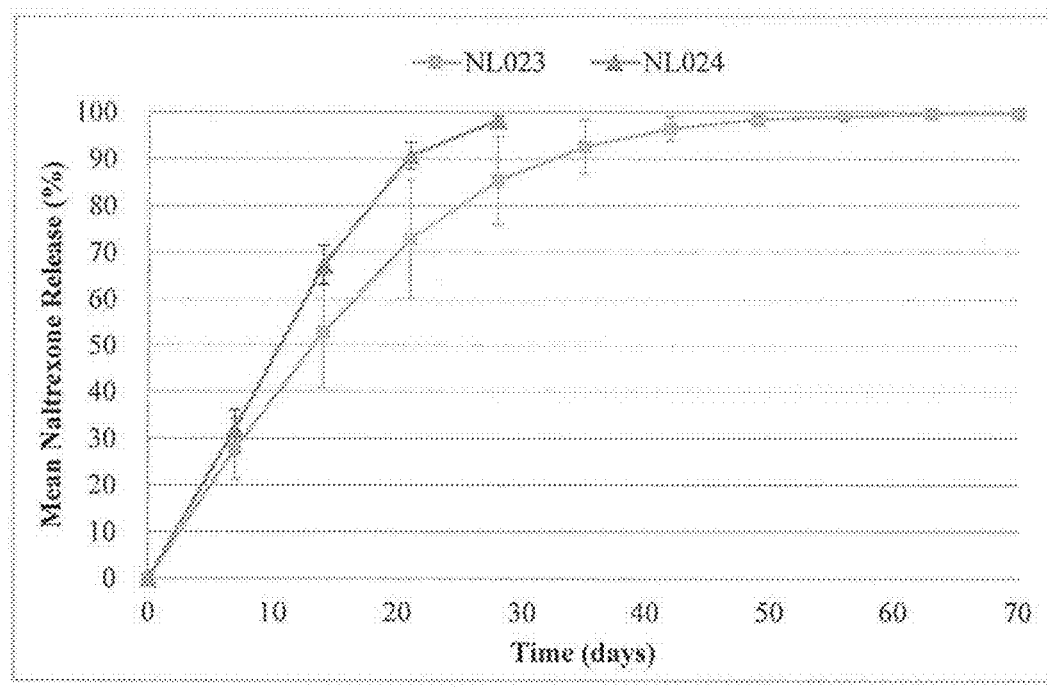
FIG. 7 shows mean naltrexone releasing profiles after subcutaneous injection of NL023 and NL024 at the dose of 10.3 mg naltrexone/kg in minipigs, in accordance with embodiments of the present disclosure.
Figure 8:
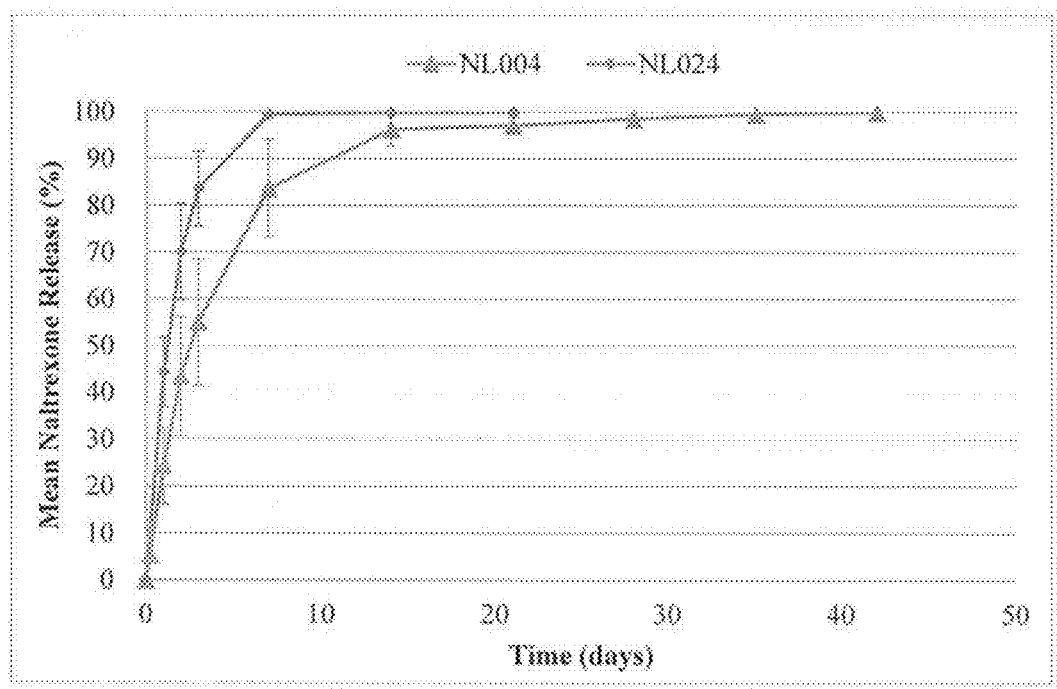
FIG. 8 shows mean naltrexone releasing profiles after subcutaneous injection of NL004 at the dose of 120 mg naltrexone/kg and NL024 at the dose of 60 mg naltrexone/kg in rats, in accordance with embodiments of the present disclosure.

The In vivo releasing profiles of the formulation NL023 and NL024 in minipigs were shown in Table 8 and FIG. 7. The In vivo releasing profiles of the formulation NL004 and NL024 in rats were shown in Table 9 and FIG. 8. The releasing profiles in two different animal models showed that the formulations could constantly release naltrexone for various periods from one week to 2 months.

TABLE 8

Mean naltrexone releasing percentages after subcutaneous injection of NL023 and NL024 at the dose of 10.3 mg naltrexone/kg in minipigs

|  | NL023 (10.3 mg/kg) | | NL024 (10.3 mg/kg) | |
|---|---|---|---|---|
| Time (days) | Mean naltrexone release (%) | S.D. (n = 3) | Mean naltrexone release (%) | S.D. (n = 3) |
| 0 | 0 | 0 | 0 | 0 |
| 7 | 27.73 | 6.54 | 32.00 | 4.11 |
| 14 | 52.89 | 12.12 | 67.32 | 4.16 |
| 21 | 72.80 | 12.69 | 90.65 | 2.85 |
| 28 | 85.38 | 9.43 | 98.30 | 1.00 |
| 35 | 92.55 | 5.73 | — | — |
| 42 | 96.49 | 2.61 | — | — |
| 49 | 98.43 | 1.09 | — | — |
| 56 | 99.04 | 0.06 | — | — |
| 63 | 99.57 | 0.23 | — | — |
| 70 | 99.68 | 0.00 | — | — |

TABLE 9

Mean naltrexone releasing percentages after subcutaneous injection of NL004 at the dose of 120 mg naltrexone/kg and NL024 at the dose of 60 mg naltrexone/kg in rats

|  | NL004 (120 mg/kg) | | NL024 (60 mg/kg) | |
|---|---|---|---|---|
| Time (days) | Mean naltrexone release (%) | S.D. (n = 3) | Mean naltrexone release (%) | S.D. (n = 4) |
| 0 | 0 | 0 | 0 | 0 |
| 0.25 | 5.39 | 1.79 | 11.04 | 1.69 |
| 1 | 24.34 | 8.20 | 44.34 | 7.41 |
| 2 | 43.37 | 12.66 | 70.06 | 10.30 |
| 3 | 54.96 | 13.60 | 83.52 | 8.01 |
| 7 | 83.63 | 10.41 | 99.45 | 0.36 |
| 14 | 96.23 | 3.57 | 99.76 | 0.14 |
| 21 | 97.05 | 1.73 | 99.92 | 0.05 |
| 28 | 98.47 | 0.94 | — | — |
| 35 | 99.44 | 0.36 | — | — |
| 42 | 99.88 | 0.09 | — | — |

Therefore, the injectable sustained release formulations of the present disclosure could maintain long therapeutic duration and provide high drug loading after a single dose administration. The subcutaneous injection administration system could be less painful than intramuscular injection and provide relatively small volume of the formulation. Furthermore, the dissolution release profiles and pharmacokinetic profiles in minipigs of the formulations also proved that the naltrexone derivatives may be used as the prodrugs and converted into the parent compound, naltrexone, for the treatment at least one week to several months.

While the disclosure has been described with respect to a limited number of embodiments, those skilled in the art, having the benefit of this disclosure, will appreciate that other embodiments can be devised which do not depart from the scope of the present disclosure as disclosed herein. Accordingly, the scope of the present disclosure should be defined only by the attached claims.

What is claimed is:

1. An injectable sustained release pharmaceutical formulation, comprising 3-acyl-naltrexone or a pharmaceutically acceptable salt thereof, and a biocompatible organic solvent,
   wherein the 3-acyl-naltrexone comprises an alkylcarbonyl group or an arylcarbonyl group, and wherein the alkylcarbonyl group has an alkyl portion comprising a straight chain or a branched chain having 2 to 20 carbon atoms, and the arylcarbonyl group has an aryl portion comprising an aromatic group having 6 to 18 carbons; and
   wherein the biocompatible organic solvent is selected from the group consisting of N-methyl-2-pyrrolidone, N,N-dimethylacetamide, and a combination thereof.

2. The injectable sustained release pharmaceutical formulation according to claim 1, wherein the 3-acyl-naltrexone or the pharmaceutically acceptable salt thereof is present in an amount of between 1% and 99% by weight based on a total weight of the injectable sustained release pharmaceutical formulation.

3. The injectable sustained release pharmaceutical formulation according to claim 1, further comprising a biocompatible polymeric material, wherein the biocompatible polymeric material is selected from the group consisting of poly (D, L-lactide) (PLA), poly (D, L-lactide/glycolide) (PLGA) and a combination thereof.

4. The injectable sustained release pharmaceutical formulation according to claim 3, wherein the biocompatible polymeric material is present in an amount of between 1% and 10% by weight, based on a total weight of the injectable sustained release pharmaceutical formulation.

5. A method for treating opioid use disorder or alcoholism, comprising administering the injectable sustained release pharmaceutical formulation according to claim 1 to a subject in need thereof, wherein the injectable sustained release pharmaceutical formulation provides a sustained release profile for at least one week.

6. The method according to claim 5, wherein the injectable sustained release pharmaceutical formulation is administered by subcutaneous, intramuscular or intradermal injection.

* * * * *